United States Patent [19]

Saville

[11] Plant 5,091

[45] Aug. 23, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 328,419

[22] Filed: Dec. 7, 1981

[51] Int. Cl.[3] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

A new miniature rose variety of bright red coloring long lasting on the plant and as a cut flower.

1 Drawing Figure

The present invention relates to a new and distinct variety of rose plant of the miniature rose class, named Savswat, which was originated by my crossing as seed parent the rose known as "Sheri Anne" (U.S. Plant Pat. No. 3,826) and the rose known as "Watercolor" (U.S. Plant Pat. No. 4,031) as pollen parent.

Among the novel characteristics possessed by this new variety which distinguish it from its parents and all other varieties of which I am aware are cardinal red buds opening to heavily petalled red flowers having cardinal red outer petals grading to spinel red inner petals and a very vigorous plant with abundant foliage. Middle and inner petals have sharply pointed petal apices. Flowers are exceptionally long lasting on the plant and as a cut flower. Asexual reproduction by budding of the new variety as performed in Essex County, Mass., shows that the foregoing and other distinguishing characteristics come true to form and are established and transmitted through succeeding propagations.

The accompanying drawings shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (RHSCC). The terminology used in color description herein refers to plate numbers in the aforementioned color chart, e.g., "53A" is plate 53A of The Royal Horticultural Society Color Chart.

Parentage: Seedling.
*Seed parent.*—"Sheri Anne".
*Pollen parent.*—"Watercolor".
Class: Miniature.

The following observations are made of specimens grown outdoors in Essex County, Mass. during the month of September.

FLOWER

Blooming habit: Recurrent.

A. Bud:
(1) *Size.*—Medium to large (for a miniature).
(2) *Form.*—Ovate.
(3) *Color.*—When sepals first divide — Cardinal red 53A. When petals begin to unfurl — 51A to 51B.

(4) *Sepals.*—Smooth, slightly foliated, longer than bud.
(5) *Peduncle.*—Length — $1\frac{1}{4}$ to $1\frac{1}{2}$ inches. Aspect — straight. Strength — erect. Color — reddish green.

B. Bloom:
(1) *Size.*—Average size when fully expanded — about $1\frac{1}{2}$ inches.
(2) *Borne.*—Singly and sprays of 4 to 6 blooms.
(3) *Form.*—High centered at first, becoming flat.
(4) *Petalage.*—Number of petals under normal conditions — about 60 to 70.
(5) *Color.*—As cardinal red buds 53A unfurl outer petal underside surface 51A to 51B is seen. Outer petal tip surfaces are deeper red while coloring of inner petals tends to lighter red coloring near 52D in open bloom with petals in between maintaining a red gradient of middle tonality. Color of blooms $\frac{1}{3}$ to $\frac{1}{2}$ open displays more uniform red coloring 53C (outer petals) to Spinel red 54A (inner petals). Pale pink to whitish petal edge, particularly at petal apex, is conspicuous.

C. Petals:
(1) *Texture.*—Thick.
(2) *Appearance.*—Velvety to satiny becoming matte.
(3) *Form.*—Obovate with mucronate apex (sharply pointed petals, particularly on middle and inner petals).
(4) *Arrangement.*—Regularly arranged.
(5) *Petaloids in center.*—Medium.
(6) *Persistence.*—Drop off cleanly.
(7) *Fragrance.*—Slight.
(8) *Lasting quality.*—Very long lasting on plant and as cut flower.

REPRODUCTIVE ORGANS

A. Stamens, filaments and anthers:
(1) *Arrangement.*—Irregular, intermixed.
(2) *Color.*—17B.

B. Pollen:
*Color.*—17A.

C. Styles: Uneven length, intermixed with stamens and petaloids.

D. Stigmas:
*Color.*—1D.

E. Hips:
*Shape.*—Round.
*Size.*—About $\frac{5}{8}$ inch.
*Color.*—33B.

*Do seeds protrude?*—No.

PLANT

A. Form: Upright, compact.

B. Growth: Very vigorous.

*Height attained.*—About 14 inches.

C. Foliage: Compound 5 to 7 leaflets.

(1) *Size.*—Medium to large.

(2) *Quantity.*—Abundant.

(3) *Color.*—New foliage: Upper side — near to 148B; Under side — near to 148C. Old foliage: Upper side — near 147D to 147A; Under side — near 148C.

(4) *Shape.*—Oval.

(5) *Texture.*—Upper side is slightly glossy and under side is dull.

(6) *Edge.*—Serrated.

(7) *Serration.*—Serrulate.

(8) *Leaf stem.*—Color — near to 146A. Under side — near 146C.

(9) *Stipules.*—Relatively long.

(10) Resistance to disease.—Blackspot — Good. Mildew — Fair.

D. Wood:

(1) *New wood.*—Color — near 138A. Bark — smooth.

(2) *Old wood.*—Color — near 138A. Bark — smooth.

E. Thorns:

(1) *Thorns.*—Quantity (main stalk): ordinary. On laterals from stalk — ordinary. Form — straight, thin, pointed, angled slightly downward. Length — medium. Color — near 186A. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by bright red flowers of heavy petalage featuring cardinal red outer petals grading to spinel red inner petals with sharply pointed petal apices particularly on middle and inner petals and flowers which are very long lasting on the plant and after cutting.

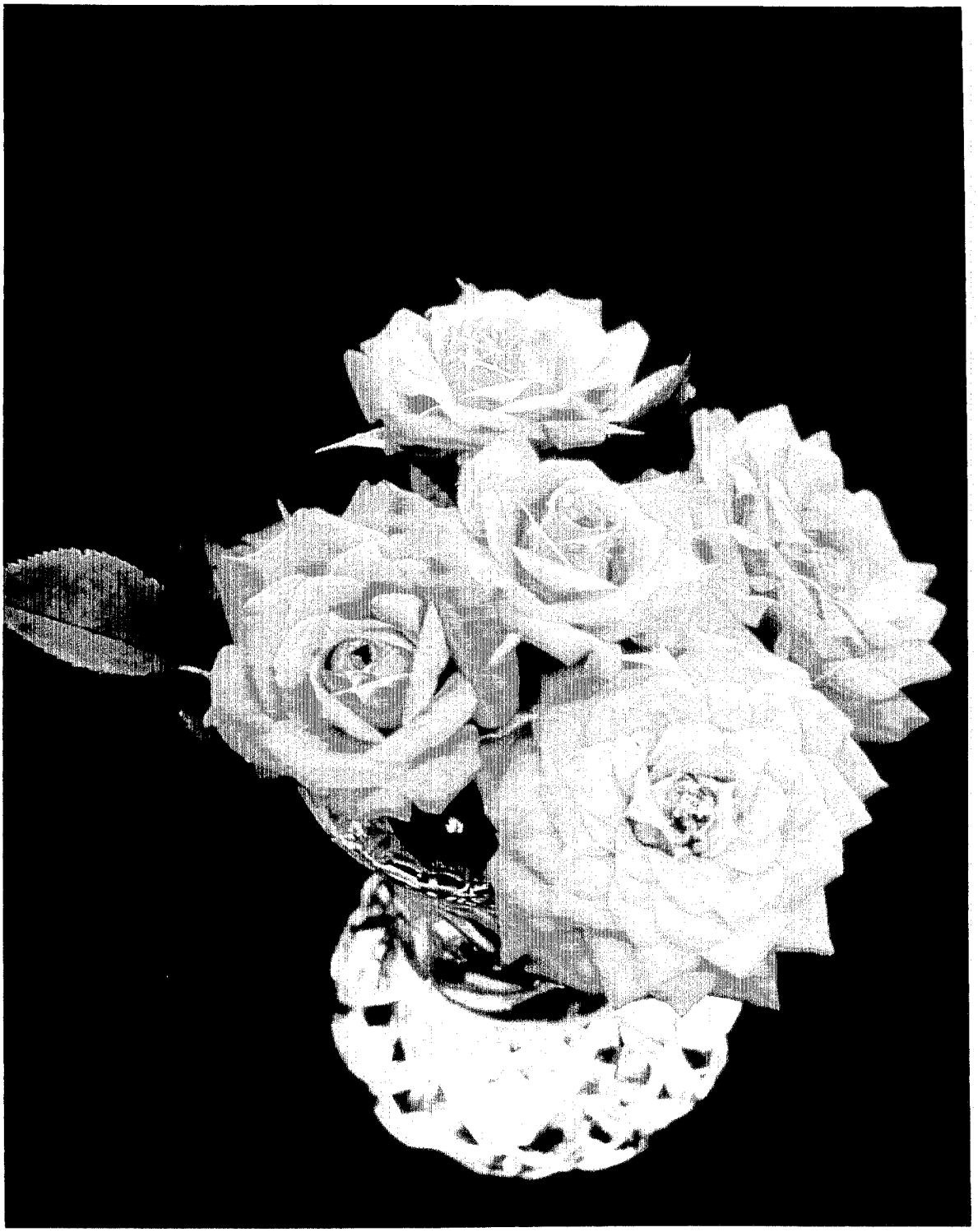

* * * * *